United States Patent [19]

Hunter et al.

[11] Patent Number: 4,935,404
[45] Date of Patent: Jun. 19, 1990

[54] PHOSPHORUS CONTAINING PEPTIDES, PHARMACEUTICAL COMPOSITIONS AND METHOD OF TREATING COLLAGENOLYTIC CONDITIONS

[75] Inventors: David J. Hunter; Roger E. Markwell; Robert W. Ward, all of Essex, England

[73] Assignee: Beecham Group p.l.c. of Beecham House, Brentford, England

[21] Appl. No.: 270,085

[22] Filed: Nov. 14, 1988

[30] Foreign Application Priority Data

Nov. 14, 1987 [GB] United Kingdom ................. 8726714

[51] Int. Cl.$^5$ ........................ A61K 37/02; C07K 5/02; C07K 5/06
[52] U.S. Cl. .......................................... 514/19; 562/15
[58] Field of Search .................... 514/19; 260/502.5 E

[56] References Cited

U.S. PATENT DOCUMENTS

| | | | |
|---|---|---|---|
| 3,950,402 | 4/1976 | Franz | 260/502.5 E |
| 4,016,148 | 4/1977 | Atherton et al. | 260/502.5 E |
| 4,213,969 | 7/1980 | Baylis et al. | 260/502.5 E |
| 4,331,591 | 5/1982 | Baylis | 260/502.5 E |
| 4,389,349 | 6/1983 | Cho et al. | 260/502.5 E |
| 4,661,298 | 4/1987 | Mirviss et al. | 260/502.5 E |
| 4,804,500 | 2/1989 | Miller | 260/502.5 E |

OTHER PUBLICATIONS

Review Article Collagenase Inhibtors: Their Design and Potential Therapeutic Use.
W. H. Johnson, N. A. Roberts and N. Borkakoti, Roche Products Limited, P.O. Box 8, Welwyn Garden City, Hertz AL7 3AY, UK.
(Received Jun. 9, 1987), J. Enzyme Inhibition, 1987, vol. 2, pp. 1-22; 1987 Harwood Academic Publishers GmbH Great Britain.

Primary Examiner—Lester L. Lee
Attorney, Agent, or Firm—Hopgood, Calimafde, Kalil, Blaustein & Judlowe

[57] ABSTRACT

Novel compounds of the formula (I), a process for their preparation and their use as collagenase inhibitors are described:

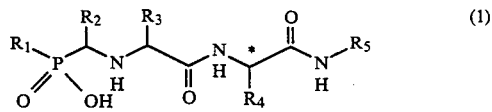

in which $R_1$ is hydrogen or hydroxy; $R_2$ is hydrogen or alkyl; $R_3$ is $C_{3-6}$ alkyl; $R_4$ is hydrogen, alkyl, —$CH_2$—Z where Z is optionally substituted phenyl or heteroaryl, or $R_4$ is a group

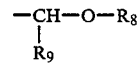

where $R_8$ is hydrogen, alkyl or —$CH_2$—Ph where Ph is optionally substituted phenyl, and $R_9$ is hydrogen or alkyl; and $R_5$ is hydrogen or alkyl.

12 Claims, No Drawings

PHOSPHORUS CONTAINING PEPTIDES, PHARMACEUTICAL COMPOSITIONS AND METHOD OF TREATING COLLAGENOLYTIC CONDITIONS

The present invention relates to novel phosphorus derivatives, processes for their preparation and their use in medicine. In particular, the present invention relates to their use as collagenase inhibitors for treating arthritic and other diseases.

The range of therapeutic applications of the collagenase inhibitors described hereinafter reflects the fundamental role of collagen within the connective tissue matrix throughout the body, and extends to many diseases not primarily due to collagen destruction but involving tissue remodelling, as these will also be susceptible to clinical intervention with collagenase inhibitors. In particular, inhibition of collagenases released from synovial and skin fibroblasts, chondrocytes, peripheral mononuclear cells, keratinocytes and gingival tissue, as well as inhibition of collagenase stored in polymorphonuclear leucocytes (PMNLs) should be of therapeutic value, and the present compounds are envisaged as having application against these and related mammalian collagenases.

Specifically, collagenase inhibitors will provide useful treatments for arthritic diseases such as rheumatoid arthritis and osteoarthritis, soft tissue rheumatism, polychondritis and tendonitis; for bone resorption diseases such as osteoporosis, Paget's disease, hyperparathyroidism and cholesteatoma; for the recessive classes of dystrophic epidermolysis bullosa; for periodontal disease and related consequences of gingival collagenase production or of PMNL collagenase production following cellular infiltration to inflamed gingiva; for corneal ulceration e.g. that induced by alkali or other burns, by radiation, by vitamin E deficiency or retinoid deficiency; and for systemic chemotherapy of cancer, where collagenase has been implicated in the neovascularization required to support tumour survival and growth, and in the penetration of tumour cells through the basement membrane of the vascular walls during metastasis. A collagenase inhibitor may also be of use in some post-operative conditions such as colonic anastomosis in which collagenase levels are raised.

As a particular example of the therapeutic value of collagenase inhibitors, chronic arthritic diseases lead to extensive loss of the collagen and proteoglycan components within the cartilage and bone of the affected joints. Neutral metalloproteases, especially collagenases and proteoglycanases, are currently thought to be the major enzymes involved.

These enzymes have been detected in extracts of synovial and cartilage tissue, and have also been extensively studied in tissue cultures of these organs. Apart from control of the biosynthesis or secretion of the enzymes, the most significant natural regulation of the activity of collagenase and protoglycanase in the normal and diseased state, is considered to be the production of inhibitors such as the Tissue Inhibitor of Metalloproteases (TIMP) and $\alpha_2$-macroglobulin. An imbalance between the levels of proteolytic enzymes and natural inhibitors will allow destruction of the connective tissue components to proceed.

Restoration of the enzyme-inhibitor balance by treatment with synthetic inhibitors of collagenase thus offers a useful therapy for a wide range of connective tissue diseases in which collagenolytic activity is a causative or major contributory factor.

European Patent No. 0054862 discloses a class of substituted dipeptides having useful enkephalinase inhibiting activity.

Novel structurally related compounds have now been discovered, which are collagenase inhibitors and thus of potential utility in the treatment of diseases in which collagenolytic activity and tissue remodelling is implicated.

According to the present invention there is provided a compound of general formula (I), or a salt, solvate or hydrate thereof:

$$R_1\underset{O}{\underset{\|}{P}}(OH)-CH(R_2)-NH-CH(R_3)-C(O)-NH-CH^*(R_4)-C(O)-NH-R_5 \quad (I)$$

in which, $R_1$ is hydrogen or hydroxy;

$R_2$ is hydrogen or alkyl;

$R_3$ is $C_{3-6}$ alkyl;

$R_4$ is hydrogen, alkyl, —$CH_2$—Z where Z is optionally substituted phenyl or heteroaryl, or $R_4$ is a group $$-\underset{R_9}{\underset{|}{CH}}-O-R_8$$

where $R_8$ is hydrogen, alkyl or —$CH_2$—Ph where Ph is optionally substituted phenyl and $R_9$ is hydrogen or alkyl; and $R_5$ is hydrogen or alkyl.

Unless otherwise specified, each alkyl group is preferably a $C_{1-8}$ group, more preferably $C_{1-6}$, and may be a straight chain or branched.

Optional substituents for phenyl and heteroaryl groups may be selected from OH, $C_{1-6}$ alkyl, $C_{1-6}$ alkoxy and halogen.

Z when heteroaryl includes 5- or 6-membered monocyclic and 9- or 10-membered bicyclic heteroaryl of which 9- or 10-membered bicyclic heteroaryl is preferred.

In addition, 5- or 6-membered monocyclic and 9- or 10-membered bicyclic heteroaryl preferably contain one or two heteroatoms selected from nitrogen, oxygen and sulphur which in the case of there being more than one heteroatom may be the same or different. When Z is 9- or 10-membered bicyclic heteroaryl the two rings are preferably fused with one 5- or 6-membered ring containing a single heteroatom.

$R_1$ is preferably hydroxy.

Examples of $R_2$ include hydrogen, methyl, ethyl and isopropyl.

$R_2$ is preferably methyl or ethyl.

$R_3$ is preferably a $C_4$ alkyl group, such as n-butyl, iso-butyl or sec-butyl, especially iso-butyl.

$R_4$ is preferably benzyl, 4-hydroxybenzyl, $C_{1-6}$ alkoxybenzyl such as 4-methoxybenzyl or 9- or 10-membered fused bicyclic heteroarylmethyl such as 3-indolylmethyl.

Preferred values for $R_5$ are methyl and ethyl, especially methyl.

The compounds of formula (I) may form salts with bases e.g. sodium hydroxide. The compounds of formula (I) have a basic nitrogen atom and may form acid addition salts e.g. with hydrochloric acid. Such compounds form part of the present invention.

Where compounds of formula (I), or salts thereof, form solvates or hydrates, these also form an aspect of the invention.

The compounds of formula (I) may have one, two or three asymmetric centres and therefore exist in more than one stereoisomeric form. The invention extends to all such forms and to mixtures thereof, including racemates, and diastereoisomeric mixtures.

Preferred isomers are those having the S configuration at the chiral centre marked with an asterisk in formula (I).

The compounds of formula I or their salts, solvates or hydrates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% by weight, preferably 75%, more preferably 90% and still more preferably 95% or 99% or more of the compound of formula I or its salt or solvate.

Compounds of formula (I) or their salts, solvates or hydrates may be isolated as crystalline solids or in the form of foams or gums.

One preferred pharmaceutically acceptable form is the crystalline form.

The present invention provides the compounds of formula (I) or pharmaceutically acceptable salts, solvates or hydrates thereof for use as active therapeutic agents, particularly as agents for treatment of musculoskeletal disorders resulting from collagenolytic activity, particularly arthritic diseases, and tissue remodelling, and for use in the systemic chemotherapy of cancer.

The present invention also provides a process for the preparation of a compound of formula (I) which comprises cleaving a group $R_{10}$ from a compound of formula (II):

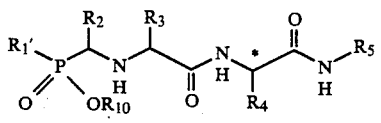

wherein $R_{10}$ is alkyl or optionally substituted benzyl and $R_1'$ is $R_1$ or a group or atom convertible thereto, and $R_2$, $R_3$, $R_4$ and $R_5$ are as defined in formula (I), and where necessary, converting $R_1'$ to $R_1$.

Cleavage of $R_{10}$ may be carried out in aqueous acid or alkali or using a trimethylsilyl halide, preferably bromotrimethylsilane, in an inert solvent, for example dichloromethane. Benzyl esters may alternatively be removed by hydrogenolysis or other standard debenzylation procedures.

Where the compound of formula (I) is a phosphonic acid derivative ($R_1$=OH), $R_1'$ in a compound of formula (II) is conveniently alkoxy for example methoxy or ethoxy, or benzyloxy, such that cleavage of both $R_1'$ and $R_{10}$ is conveniently effected in a single reaction.

Compounds of formula (II) may be prepared by treating a compound of formula (III):

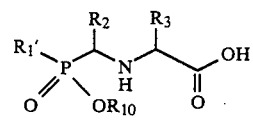

in which $R_1'$, $R_2$, $R_3$, and $R_{10}$ are as defined in formula (II), with a compound of formula (IV):

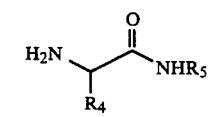

in which $R_4$ and $R_5$ are as defined in formula (I)

The reaction is preferably carried out in the presence of a coupling agent, such as dicyclohexylcarbodiimide or 1-ethyl-3-[3-(dimethylamino)propyl]carbodiimide hydrochloride in the presence of 1-hydroxybenzotriazole, or using 1,1'-carbonyldiimidazole, in an inert solvent such as dichloromethane or acetonitrile.

The intermediate compounds of formula (III) may be prepared by treating a compound of formula (V) or a salt thereof:

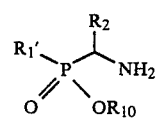

in which $R_1'$, $R_2$ and $R_{10}$ are as defined in formula (II), with a compound of formula (VIA) or (VIB) or a salt thereof:

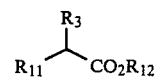

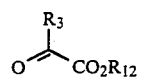

in which $R_3$ is as defined in formula (I), $R_{11}$ is a leaving group such as halogen, methanesulphonyloxy or trifluoromethanesulphonyloxy and $R_{12}$ is hydrogen or a carboxyl protecting group, and thereafter removing an $R_{12}$ carboxyl protecting group.

When a compound of formula (VIB) is used, the reductive amination may be carried out by hydrogenation over a noble metal catalyst such as palladium on carbon or by reaction with sodium cyanoborohydride at pH 6 to 7. Lower alkyl alcohol solvents such as methanol and ethanol are suitable for both reactions. These reactions may be carried out in the presence of molecular sieves.

A hydrogenation reaction is preferred but this process precludes the use of a compound of formula (VIB) in which $R_{12}$ is benzyl. Preferably a carboxyl protecting group is a methyl or ethyl ester. Ester protecting groups may be removed under standard basic hydrolysis conditions using dilute base such as 1 Normal sodium hydroxide in methanol.

When the compound of formula (V) is in the form of the free base, the compound of formula (VIB) is suitably an α-keto ester ($R_{12}$=H).

When the compound of formula (V) is a salt, such as the hydrochloride salt, the compound of formula (VIB) is suitably a salt of an α-keto acid ($R_{12}$=H), for example the sodium salt.

The preparation of compounds of formula (III) using a compound of formula (VIA) may be carried out under standard alkylation conditions. A halogen leaving group is preferably bromine and an oxygen-based leaving group is preferably trifluoromethanesulphonyloxy.

Compounds of formula (III) in which $R_1'$ is alkoxy may alternatively be prepared by condensing a compound of formula (VII) or a salt thereof:

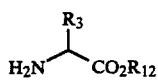

(VII)

in which $R_3$ is as defined in formula (I) and $R_{12}$ is a carboxyl protecting group with an aldehyde, $R_2$—CHO in which $R_2$ is as defined in formula (I) and treating the condensation product with an appropriate dialkyl phosphite, for example dimethyl phosphite, and thereafter removing the carboxyl protecting group. The carboxyl group is conveniently protected as an alkyl or benzyl ester which may be removed using standard hydrolysis or hydrogenation conditions.

Intermediate compounds of formula (V) are either known compounds or may be prepared from known aminomethyl phosphinic acid derivatives using standard procedures to introduce the variables $R_1'$ and $R_{10}$ as required. Protection of the amine function during these reactions may be necessary.

Introduction of an $R_{10}$ methyl group may be effected by reaction with diazomethane in a suitable inert solvent.

The compounds of formulae (IV) and (VII) are either known amino acid derivatives or can be made from these derivatives by known methods. Compounds of formula (VIA) and (VIB) are either known compounds or may be prepared from known compounds by known methods.

The intermediates of formulae (II), (III), and certain intermediates of formula (V) disclosed herein are novel compounds and form an aspect of the present invention as do the described processes for their preparation.

Where obtainable, pharmaceutically acceptable salts of the compounds of formula (I) may be formed conventionally by reaction with the appropriate acid or base. Solvates may be formed by crystallization from the appropriate solvent.

As mentioned previously, the compounds of formula (I) exist in more than one diastereoisomeric form. Where the processes of the invention produces mixtures thereof, the individual isomers may be separated one from another by chromatography e.g. HPLC.

Alternatively, separate diastereoisomeric compounds of formula (I) can be obtained by using stereoisomerically pure starting materials or by separating desired isomers of intermediates at any stage in the overall synthetic process, and converting these intermediates to compounds of formula (I).

The present invention further provides a pharmaceutical composition, which comprises a compound of formula (I), or a pharmaceutically acceptable salt or solvate thereof, and a pharmaeutically acceptable carrier.

A composition of this invention is useful in the treatment of rheumatism and arthritis and in the treatment of other collagenolytic conditions.

A composition of the invention, which may be prepared by admixture, may contain a diluent, binder, filler, disintegrant, flavouring agent, colouring agent, lubricant, preservative in conventional manner. These conventional excipients may be employed in conventional manner, for example as in the preparation of compositions of related peptide enzyme inhibitors, such as the ACE inhibitor enalapril.

A composition of the invention may be adapted for oral, topical, percutaneous, rectal or parenteral-intravenous, intramuscular, sub-cutaneous, intradermal or intra-articular-administration but oral administration is preferred.

Preferably, a pharmaceutical composition of the invention is in unit dosage form and in a form adapted for use in the medical or veterinarial fields. For example, such preparations may be in a pack form accompanied by written or printed instructions for use as an agent in the treatment or prophylaxis of any of the disorders mentioned above.

The suitable dosage range for the compounds of the invention may vary from compound to compound and may depend on the condition to be treated. It will also depend, inter alia, upon the relation of potency to absorbability and the mode of administration chosen.

The compound or composition of the invention may be formulated for administration by any route, the preferred route depending upon the disorder for which treatment is required, and is preferably in unit dosage form or in a form that a human patient may administer to himself in a single dosage.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tableting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tableting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients. For example, in a hard gelatin capsule containing the required amount of a compound of the invention in the form of a powder or granulate in intimate mixture with a lubricant, such as magnesium stearate, a filler, such as microcrystalline cellulose, and a disintegrant, such as sodium starch glycollate.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository or for parenteral administration in an injectable form. For injection, for example by intra-articular injection as poorly dispersed depot stores, the compounds of the invention may be presented in an aqueous or non-aqueous solution, suspension or emulsion in a pharmaceutically acceptable liquid, e.g. sterile pyrogen-free water or a parenterally acceptable oil or a mixture of liquids, which may contain bacteriostatic agents, anti-oxidants or other preservatives, buffers or solutes to render the solution isotonic with the blood, thickening agents, suspending agents or other pharmaceutically acceptable additives. Such forms will be presented in sterile unit dose form such as ampoules or disposable injection devices or in multi- dose forms such as a bottle from which the appropriate dose may be withdrawn or a solid form or concentrate which can be used to prepare an injectable formulation.

For topical and percutaneous administration, the preparations may also be presented as an ointment, cream, lotion, gel, spray, aerosol, wash, skin paint or patch.

A unit dose for inflammatory diseases will generally contain from 10 to 1000 mg and preferably will contain from 10 to 500 mg, in particular 10, 50, 100, 150, 200, 250, 300, 350, 400, 450 or 500 mg. The composition may be administered once or more times a day, for example 2, 3 or 4 times daily, so that the total daily dose for a 70 kg adult will normally be in the range 10 to 3000 mg. Alternatively, in particular for injection, the unit dose will contain from 2 to 200 mg of a compound of the invention and be administered in multiples, if desired, to give the desired daily dose.

The present invention additionally provides a method of treating a collagenolytic condition such as rheumatism and/or arthritic conditions, or cancer, or other diseases in which enzyme-mediated breakdown of connective tissue components plays a role in mammals, such as humans, which comprises administering an effective amount of a compound of formula (I) or a pharmaceutically acceptable salt, solvate or hydrate thereof, to the mammal.

The present invention also provides the use of a compound of formula (I) or a pharmaceutically acceptable salt, solvate or hydrate thereof, for the manufacture of a medicament for use as an active therapeutic substance, particularly in the treatment of collagenolytic conditions, such as rheumatism, cancer, bone disorders, skin diseases, periodontal disease or corneal ulceration, in mammals.

The following Descriptions and Examples illustrate the preparation of compounds of the invention and the subsequent biological data illustrates their pharmacological activity. All temperatures are expressed in °C.

DESCRIPTION 1

N-(1-Phosphonoethyl)-leucine triethyl ester (D1)

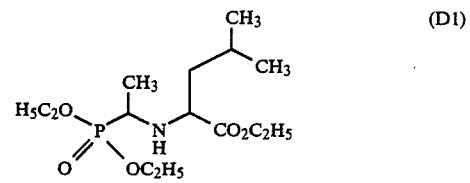

[1-[(Phenylmethyl)amino]ethyl]phosphonic acid, diethyl ester (2.76 g) [prepared by the procedure of F. R. Atherton et al. J. Med. Chem. 29, 29, 1986] was dissolved in ethanol (100 ml) and hydrogenated over 10% palladium on charcoal at atmospheric pressure. Ethyl (4-methyl-2-oxo)pentanoate (1.58 g) and molecular sieves were added and the hydrogenation continued for 48 h. The catalyst was removed by filtration and the filtrate evaporated in vacuo to yield a colourless oil, which was chromatographed on silica gel, eluting with ethyl acetate, to give the title compound as a mixture of isomers (0.83 g).

DESCRIPTION 2

N-(1-Diethoxyphosohinylethyl)-leucine (D2)

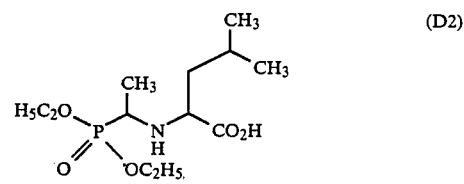

Method A

N-(1-Phosphonoethyl)-leucine triethyl ester (D1) (0.81 g) was dissolved in methanol (30 ml) and treated with sodium hydroxide (0.2 g) in water (15 ml). After 24 h, the solution was acidified with 5N HCl and extracted with dichloromethane. The organic extracts were dried over anhydrous sodium sulphate and the solvent removed in vacuo to give the title compound (0.66 g).

Method B

A solution of the hydrochloride salt of [1-(phenylmethyl)amino]ethyl]phosphonic acid diethyl ester (15 g) dissolved in ethanol (400 ml) was hydrogenated over 10% palladium on charcoal at atmospheric pressure until conversion to the primary amine was complete. 4-Methyl-2-oxopentanoic acid sodium salt was then added in the minimum volume of water and the hydrogenation continued for 3 days. The catalyst was removed by filtration and the filtrate evaporated in vacuo to give a colourless oil which was then taken up in chloroform and washed with water (30 ml) followed by dilute citric acid (2×30 ml) and a further aqueous wash. After drying (Na2SO4) the chloroform layer was evaporated to dryness to give the title compound as a sticky white solid having the same spectroscopic properties as the material obtained in Method A.

DESCRIPTION 3

N-[N-(1-Phosphonoethyl)-leucyl]-N,O-dimethyl-L-Tyrosinamide, diethyl ester (D3)

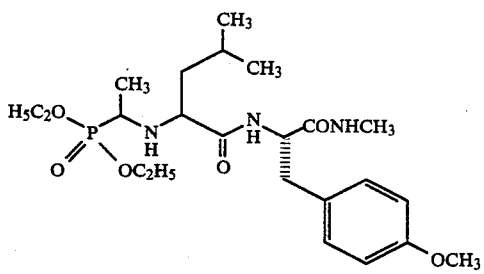

N-(1-Phosphonoethyl)-leucine diethyl ester (D2) (0.66 g) in dichloromethane (25 ml) was cooled to 0°C. 1-Hydroxybenzotriazole (0.37 g) and dicyclohexylcarbodiimide (0.57 g) were added and the solution stirred at 0° C. for ½ h. After ½ h at room temperature, the solution was cooled to 0° C. and O-methyl-L-tyrosine N-methylamide (0.52 g) in dichloromethane (25 ml) was added dropwise. The solution was stirred at room temperature for 6 h, filtered, washed with saturated sodium bicarbonate solution, dried with anhydrous sodium sulphate and evaporated in vacuo to give a colourless oil. Purification by column chromatography on silica gel, eluting with 2% methanol/chloroform gave the title compound as a colourless oil (0.8 g).

Observed M+ 485.2654; $C_{23}H_{40}N_3O_6P$ requires M 485.2650.

DESCRIPTION 4

Phenylmethylaminomethyl phosphonic acid diethyl ester (D4)

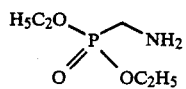

A mixture of N-benzylhexahydrotriazine (9.2 g, 0.025 mol) and diethyl phosphite (9.8 g, 0.07 mol) in dry toluene was heated at reflux for 3½ h and left stirring at room temperature overnight. The toluene was removed in vacuo and the oily residue acidified to pH 3-4 with 5N HCl and washed with ethyl acetate. The aqueous fraction was then basified with 10% sodium carbonate solution and extracted with ethyl acetate (3×50 ml). The combined organic layers were washed with water, dried and evaporated to dryness to give a yellow oil, which was purified by silica gel column chromatography eluting with ethyl acetate to give the title compound (3 g).

DESCRIPTION 5

α-Aminomethyl phosphonic acid diethyl ester (D5)

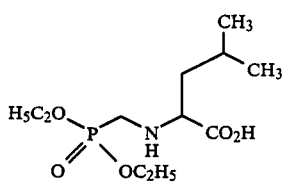

Phenylmethylaminomethyl phosphonic acid diethyl ester (D4) (1.1 g) was dissolved in ethanol (100 ml) and hydrogenated over 10% palladium on charcoal at atmospheric pressure. The catalyst was removed by filtration and the filtrate evaporated in vacuo to yield a colourless oil which was chromatographed on silica gel, eluting with 10% methanol/chloroform to give the title compound (0.60 g).

DESCRIPTION 6

N-(Diethoxyphosphinylmethyl)-leucine (D6)

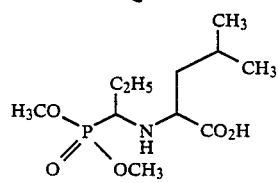

α-Aminomethyl phosphonic acid diethyl ester (D5) (600 mg) was dissolved in ethanolic HCl and evaporated in vacuo to give the hydrochloride salt. The hydrochloride salt and 4-methyl-2-oxopentanoic acid sodium salt (480 mg, 0.003 mol) were dissolved in ethanol-water (50% 80 ml) and hydrogenated over 10% palladium on charcoal at atmospheric pressure for 48 h. The catalyst was filtered off and the filtrate evaporated in vacuo. The resulting oil was triturated with chloroform, and the precipitated sodium chloride removed by filtration. The filtrate was evaporated in vacuo to give the title compound as a mixture of isomers (800 mg 89%).

DESCRIPTION 7

N-[N-(Phosphonomethyl)-leucyl]-N,O-dimethyl-L-tyrosinamide, diethyl ester (D7)

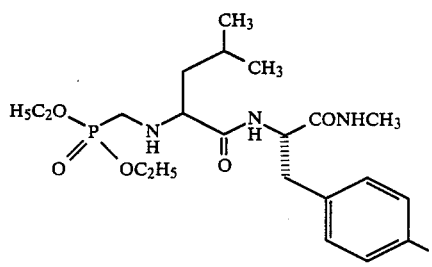

The title compound was prepared in 30% yield as a white solid from N-(diethoxyphosphinylmethyl)-leucine and O-methyl-L-tyrosine N-methylamide by the method of Description 3 using 1-ethyl-3-(3-dimethylaminopropyl)-carbodiimide hydrochloride in place of dicyclohexylcarbodiimide.

DESCRIPTION 8

N-(1-Dimethoxyphosphinylpropyl)-leucine (D8)

[1-[(Phenylmethyl)amino]propyl]phosphonic acid, dimethyl ester HCl salt (11 g) [prepared by the procedure of F. R. Atherton et al. J. Med. Chem. 29, 29, 1986] was dissolved in ethanol (200 ml) and hydrogenated over 10% palladium on charcoal at atmospheric pressure. 4-Methyl-2-oxopentanoic acid, sodium salt, (7.0 g) was added and the hydrogenation continued for 48 h. The catalyst was filtered off and the filtrate evaporated in vacuo to give an oil. The oil was triturated with chloroform, and the precipitated sodium chloride removed by filtration. The organic phase was washed with water, dried (MgSO₄), and evaporated to dryness to give the title compound as a mixture of isomers (5.83 g).

DESCRIPTION 9

N-[N-(l-Phosphonopropyl)-leucyl]-N,O-dimethyl-L-tyrosinamide, dimethyl ester (D9)

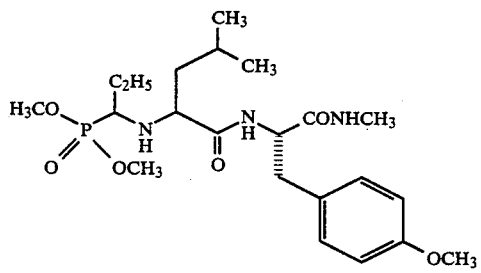

The title compound was prepared in 30% yield from N-(1-dimethoxyphosphinylpropyl)-leucine (D8) by the method of Description 3.

DESCRIPTION 10

N-(1-Dimethoxyphosphinyl-2-methylpropyl)-leucine, benzyl ester (D10)

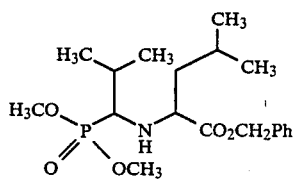

A mixture of 2-methylpropionaldehyde (1.08 g), leucine benzyl ester p-toluene sulphonate salt (5.9 g) and triethylamine (2.1 ml) in toluene (100 ml) was heated at reflux for 2 h in a Dean and Stark apparatus. Dimethyl phosphite (1.65 g) was added and the solution refluxed for 24 h. The solution was cooled and the solvent evaporated in vacuo to give a yellow oil which was chromatographed on silica gel, eluting with ethyl acetate, to give the title compound as a mixture of isomers (3.36 g).

DESCRIPTION 11

N-(1-Dimethoxyphosphinyl-2-methylpropyl)-leucine (D11)

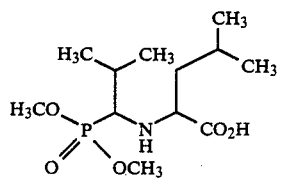

N-(1-Dimethoxyphosphinyl-2-methylpropyl)-L-leucine benzyl ester (D10) (3.3 g) was dissolved in methanol (100 ml) and hydrogenated over 10% palladium on charcoal at atmospheric pressure. The catalyst was removed by filtration and the solvent removed in vacuo to give a quantitative yield of the title compound.

DESCRIPTION 12

N-[N-(1-Phosphono-2-methylpropyl)-leucyl]-N,O-dimethyl-L-tyrosinamide, dimethyl ester (D12)

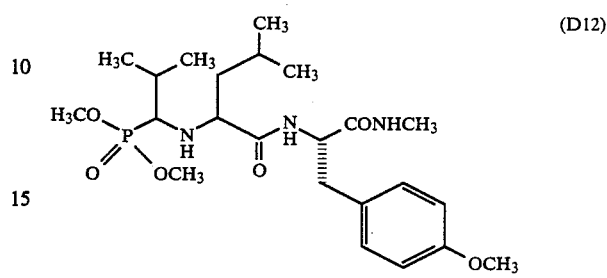

N-(1-Dimethoxyphosphinyl-2-methylpropyl)-L-leucine (D11)(2.6 g) in dichloromethane (100 ml) was cooled to 0° C. 1-Hydroxybenzotriazole (1.57 g) and 1-ethyl-3-(3-dimethylaminopropyl)carbodiimide hydrochloride (2.3 g) were added and the solution stirred at 0° C. for ½ h. O-Methyl-L-tyrosine N-methylamide (2.1 g) in dichloromethane (25 ml) was added dropwise. The solution was stirred at 0° C. for 1 h and at room temperature for 24 h. The solution was filtered, washed with water, saturated sodium bicarbonate solution and 10% citric acid solution and dried with anhydrous sodium sulphate. The solution was filtered and the solvent evaporated in vacuo to give a yellow oil. Purification by column chromatography on silica gel, eluting with 10% methanol/ethyl acetate, gave the title compound (3.8 g) as a mixture of 4 diastereoisomers.

DESCRIPTION 13

N-[N-(1-Phosphonoethyl)-leucyl]-N-methyl-L-tryptophanamide, diethyl ester (D13)

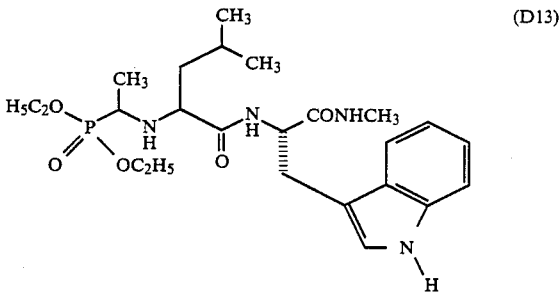

N-(1-Dimethoxyphosphinylethyl)-leucine (D2) (1 g, 0.0039 mole) in acetonitrile (20 ml) was cooled to 0°C. in an ice-bath and 1,1'-carbonyldiimidazole (0.55 g, 1 equiv.) was added. The mixture was stirred at this temperature for 1 h before adding a solution of tryptophan N-methylamide (0.81 g, 1.1 equiv.) in acetonitrile (10 ml). After stirring at room temperature overnight the solution was evaporated to dryness, taken up in ethyl acetate and washed with first dilute citric acid (×2), then water followed by dilute sodium hydroxide (×2) and finally water. The organic layer was dried with anhydrous sodium sulphate, filtered and evaporated to dryness. The resulting gum was chromatographed on silica gel (100 g) with initially chloroform as eluant rising in 1% steps to 5% methanol/chloroform. Fractions 23 to 28 contained various proportions of the four possible diastereomers, of the title compound (0.78 g in total).

EXAMPLE 1

N-[N-(1-Phosphonoethyl)-leucyl]-N,O-dimethyl-L-tyrosinamide (E1)

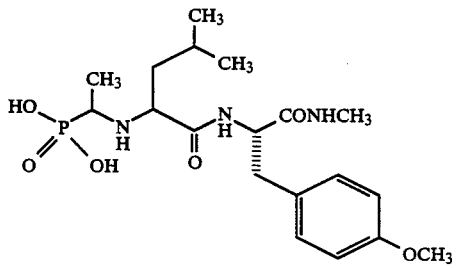

The diethyl ester (D3) (0.4 g) was dissolved in dichloromethane (10 ml) and treated with bromotrimethyl silane (5 ml). The solution was stirred at room temperature for 48 h, methanol (20 ml) was added and the solvent evaporated in vacuo to give the title compound, a yellow foam, as a mixture of 4 diastereoisomers (0.37 g) (E1). Column chromatography of the crude product (150 mg) using reverse phase silica, eluting with a gradient of 5% to 30% methanol in water, gave a faster running 1:1 mixture of 2 diastereoisomers. Isomer E1 A/B (30 mg).

δ(CDCl₃): 0.80(6H,m), 1.16(4H,m), 1.44(3H,m), 2.58(3H,m), 2.78(1H,m), 2.98(1H,m), 3.52(0.5H, broad s), 3.71(3H, s), 3.88(0.5H, broad s), 4.46(1H, m), 6.82(2H, m), 7.16(2H,m), 8.18(1H, broad s), 8.80(1H, m).

Observed FAB (M+H)+ 430. C₁₉H₃₂N₃O₆P requires M 429.

Further elution gave a slower running mixture of 2 diastereoisomers.

Isomer E1 C/D (20 mg). Observed FAB (M+H)+ 430. C₁₉H₃₂N₃O₆P requires M 429.

Separation of Isomers E1 A/B

Isomer E1 A/B was separated into single diastereoisomers by preparative HPLC on a Hamilton PRP-1 column, eluting with 25:75 methanol/0.05M aqueous ammonium acetate, pH 5.0, to give:

Isomer A: δ(CD₃OD): 0.87(3H,d), 0.92(3H,d), 1.26(3H,dd), 1.45(3H,m), 2.65(1H,dd), 2.70(3H,s), 2.84(1H,dd), 3.10(1H,dd), 3.63(1H, broad t), 3.74(3H,s), 4.60(1H,dd), 6.82(2H,d), 7.16(2H,d).

Isomer B: δ(CD₃OD): 0.90(3H,d), 0.94(3H,d), 1.25(3H,dd), 1.54(3H,m), 2.61(1H,dd), 2.69(3H,s), 2.87(1H,dd), 3.05(1H,dd), 3.75(3H,s), 4.16(1H, broad t), 4.58(1H,dd), 6.84(2H,d), 7.18(2H,d).

EXAMPLE 2

N-[N-(Phosphonomethyl)-leucyl]-N,O-dimethyl-L-tyrosinamide, disodium salt (E2)

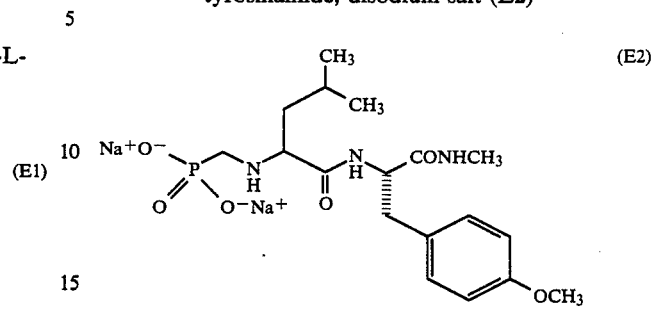

The diethyl ester (D7) (0.4 g) was dissolved in dichloromethane (10 ml) and treated with bromotrimethylsilane (1 ml). The solution was stirred at room temperature for 48 h, methanol (20 ml) was added and the solvent evaporated in vacuo to give a yellow oil. This was purified by column chromatography using reverse phase silica eluting with a gradient of 5% to 10% methanol in water to give the diacid as a white solid m.p. 260°–262° C.

Observed FAB (M+H)+ 416. C₁₈H₃₀N₃O₆P requires M 415. The diacid was stirred with sodium hydroxide solution in methanol (20 ml) for ½ h. The solvent was evaporated in vacuo to give the title compound as a white solid as a mixture of isomers (150 mg).

EXAMPLE 3

N-[N-(1-Phosphonopropyl)-leucyl]-N,O-dimethyl-L-tyrosinamide (E3)

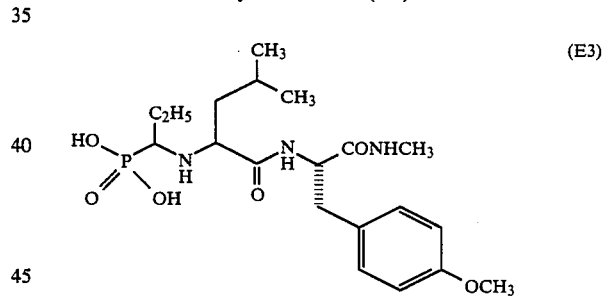

The title compound was prepared from (D9) as a mixture of 4 diastereoisomers by the method of Example 1. Column chromatography of the crude product using reverse phase silica eluting with a gradient of 1%–5% methanol in water gave a faster running mixture of 2 diastereoisomers. Isomer E3 A/B (100 mg) m.p. 160°–163° C. observed FAB (M+H)+ 444 C₂₀H₃₄N₃PO₆ requires M 443.

Further elution gave first a slower running mixture of 2 diastereoisomers. Isomer E3 C/D (80 mg) m.p. 164°–168° C. Observed FAB (M+H)+ 444 C₂₀H₃₄N₃PO₆ requires M 443. Finally a single isomer E3 D was obtained.

Separation of Isomers E3 A/B

The HPLC method described in Example 1 was used to separate the isomer E3 A/B into single diastereoisomers.

Isomer A: m.p. 160°–163° C.

δ(CD₃OD): 0.85(3H,t), 0.92(3H,d), 0.96(3H,d), 1.4–1.72 (4H,m), 1.72–1.95 (1H,m), 2.33(1H,m), 2.7(3H,s), 2.84(1H,dd), 3.03(1H,dd), 3.75 (3H,s), 4.22 (1H,brt), 4.56(1H,dd), 6.86(2H,d), 7.19(2H,d).

Isomer B: m.p. 148°-150° C.

δ(CD₃OD): 0.89(3H,d), 0.93(3H,d), 0.99(3H,t), 1.35–1.95 (5H,m), 2.68(4H,m), 2.87 (1H,dd), 3.08(1H,dd), 3.75(3H,s), 3.82 (1H,brt), 4.58(1H,dd), 6.84(2H,d), 7.17(2H,d).

EXAMPLE 4

N-[N-(1-Phosphono-2-methylpropyl)-leucyl]-N,O-dimethyl-L-tyrosinamide (E4)

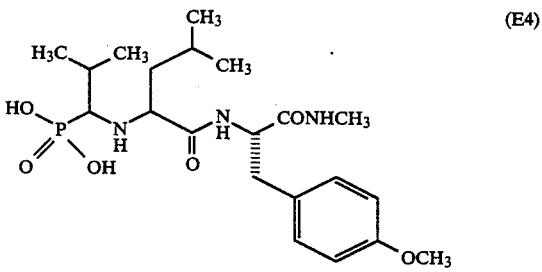

The dimethyl ester (D12) (0.5 g) was dissolved in dichloromethane (10 ml) and treated with bromotrimethylsilane (1.4 ml). The solution was stirred at room temperature for 48 h, methanol (20 ml) was added and the solvent evaporated in vacuo to give the crude product as a yellow foam. Column chromatography of the crude product using reverse phase silica, eluting with a gradient of 5% to 50% methanol in water, gave the title compound as a mixture of isomers (0.3 g).

Observed FAB (M+H)+ 458. $C_{21}H_{36}N_3O_6P$ requires M 457.

EXAMPLE 5

N-[N-(1-Phosphonoethyl)-leucyl]-N-methyl-L-tryptophanamide (E5)

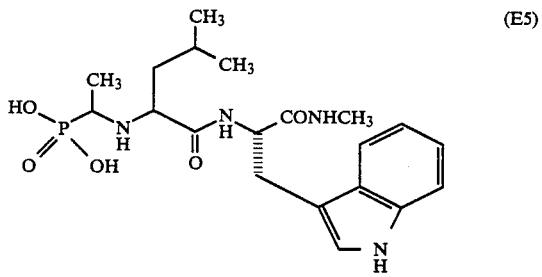

Several of the column fractions obtained in the purification of the diethyl ester of N-[N-(1-phosphonoethyl)-leucyl]-N-methyl-L-tryptophanamide (D13) were individually de-esterified by treatment with bromotrimethylsilylane.

(a) Fraction 25 of the diester (D13) (250 mg), which contained at least 3 diastereomers from its nmr spectrum was converted to the title compound by the method of E1. Purification by reverse phase chromatography with H₂O rising to 50% MeOH/H₂O gave a white solid containing 3 diastereomers by nmr, one being by far the major (80%).

Further purification by preparative HPLC on a Hamilton PRPI column [mobile phase 7.5:92.5 acetonitrile:0.05M ammonium acetate (pH5) with a flow rate of 7.0 ml/min] gave the major component as a single diastereomer. Isomer E5 A δ(CD₃OD) 0.87 (3H, d), 0.91 (3H, d), 1.22 (3H, dd), 1.3–1.7 (3H, m), 2.6–2.8 (1H, m) overlapping on 2.67, (3H, s), 3.12 (dd, 1H), 3.27 (dd, 1H partially obscured by CHD₂OD), 3.75(brt,1H) 4.72 (1H, dd), 6.95–7.08 (2H, m), 7.11 (1H, s), 7.32 (1H, d), 7.6 (1H, d).

(b) Fraction 27 of the diester (D13) (80 mg), essentially a single diastereomer from its nmr spectrum, was converted to the title compound by the method of E1. The residue after methanolic work-up was purified by chromatography on reverse phase silica gel with initally water as eluent rising to 50% methanol/water to give a single isomer. Isomer E5 B (18.8 mg). δ(CD₃OD): 0.92 (3H, d), 0.95 (3H, d), 1.18 (3H, dd), 1.58 (3H; m), 2.45 (1H, m), 2.72 (3H, s), 3.12 (1H, dd), 3.30 (1H, m partially obscured by CHD₂OD signal), 4.25 (1H, t), 7.07 (2H, m), 7.18 (1H, s), 7.35 (1H, d), 7.66 (1H, m). In addition there are indications of a signal (m) underneath the large peak at 4.75 (HOD).

Observed FAB (M+H)+ 439 $C_{20}H_{31}N_4O_5P$ required M 438.

(c) Fraction 23 of the diester (D13) (80 mg) which from its nmr spectrum contained 2 diastereomers was converted to the title compound following the method of E1. Reverse phase chromatography with H₂O rising to 30% MeOH/H₂O as eluant gave several fractions containing two isomers, one fraction containing isomers C/D in a ratio of 3.3:1. Isomers E5 C/D (total yield 32.7 mg; the above fraction 12 mg) δ(CD₃OD): 0.5–0.7 (6H, m), 1.18–1.5 (6H, m), 2.74 (s), 2.77 (s) (together 3H), 2.93–3.20 (2H, m), 3.3–3.6 (1H, m), 4.03 (t), 4.22 (dd) (together 1H), 4.7–5.0 (1H, m), 6.95–7.15 (3H, m), 7.33 (1H, d), 7.62 (1H, d). Expansion of the region 3.9–4.4 gave the C/D ratio of 3.3:1 for the signals at 4.22 and 4.03 respectively.

COLLAGENASE INHIBITOR ASSAY

The test is performed essentially as in Cawston and Barrett Anal. Biochem. 99, 340–345 (1979). Compounds for testing are dissolved in methanol and added to purified rabbit bone collagenase or human collagenase purified from culture supernatants from the human lung fibroblast cell line, WI-38, diluted in a suitable aqueous buffer. After a 5 min pre-incubation at 37° C., the assay tubes are cooled to 4° C. and ¹⁴C-acetylated rat skin Type I collagen is added. The assay tubes are incubated at 37° C. overnight. The ¹⁴C-collagen forms insoluble fibrils which are the substrate for the enzyme.

To terminate the assay, the assay tubes are spun at 12000 rpm for 25 min. Undigested ¹⁴C-collagen remains as insoluble fibrils and is pelleted, while digested ¹⁴C-collagen remains as soluble peptides in the supernatant. A sample of the supernatant is taken for liquid scintillation counting.

The activity of collagenase inhibitors (IC₅₀: 50% inhibitory concentration) is expressed as the concentration of compound that inhibits a known (standard) concentration of enzyme by 50%, or as the % inhibition of the collagen degradation caused by the known (standard) concentration of enzyme, at a stated concentration of the compound.

The activities of representative compounds of the invention are illustrated in the tables below.

| Inhibition of rabbit bone collagenase | | |
|---|---|---|
| Example No. | Isomer | IC₅₀ (μM) |
| 1 | A/B | 0.275–1.9 (6 expts) |
| 1 | C/D | 68% Inhibition at 100 |

-continued

Inhibition of rabbit bone collagenase

| Example No. | Isomer | $IC_{50}$ ($\mu M$) | |
|---|---|---|---|
| 1 | A | 1.2 | same expt |
| 1 | B | 3.1 | |
| 1 | A/B | 1 | |
| 2 | A/B | 27 | |
| 5 | B | 0.69 | |

Inhibition of human lung fibroblast collagenase

| Example No. | Isomer | $IC_{50}$ ($\mu M$) |
|---|---|---|
| 1 | A/B | 0.51 |
| 3 | A/B | 0.33 |
| 3 | C/D | 5.4 |
| 5 | A | 0.303 |
| 5 | B | 0.426 |
| 5 | C/D | 21.9 |

We claim:

1. A compound of formula (I) or a pharmaceutically acceptable salt, solvate or hydrate thereof:

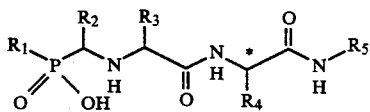

in which,
$R_1$ is hydrogen or hydroxy;
$R_2$ is hydrogen or alkyl;
$R_3$ is $C_{3-6}$ alkyl;
$R_4$ is hydrogen, alkyl, —$CH_2$—Z where Z is phenyl, phenyl substituted with a substituent selected from OH, $C_{1-6}$ alkyl, $C_{1-6}$ alkoxy or halogen, heteroalkyl, or heteroaryl substituted with a substituent selected from OH, $C_{1-6}$ alkyl, $C_{1-6}$ alkoxy or halogen, or $R_4$ is a group

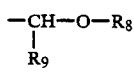

where $R_8$ is hydrogen, alkyl or —$CH_2$—Ph where Ph is phenyl or phenyl substituted with a substituent selected from OH, $C_{1-6}$ alkyl, $C_{1-6}$ alkoxy or halogen,
and $R_9$ is hydrogen or alkyl; and $R_5$ is hydrogen or alkyl.

2. A compound according to claim 1, in which $R_1$ is hydroxy.

3. A compound according to claim 1, in which $R_2$ is hydrogen, methyl, ethyl or isopropyl.

4. A compound according to claim 1, in which $R_3$ is n-butyl, iso-butyl or sec-butyl.

5. A compound according to claim 1, in which $R_4$ is benzyl, 4-hydroxybenzyl, 4-methoxybenzyl or 3-indolylmethyl.

6. A compound according to claim 1, in which $R_5$ is methyl or ethyl.

7. A compound according to claim 1, in which $R_1$ is hydroxy; $R_2$ is methyl or ethyl; $R_3$ is iso-butyl; $R_4$ is 4-methoxybenzyl or 3-indolylmethyl; and $R_5$ is methyl.

8. A compound according to claim 1, in which the chiral centre marked with an asterisk in formula (I) has the S-configuration.

9. A compound selected from the group consisting of:
N-[N-(1-Phosphonoethyl-leucyl]-N,O-dimethyl-L-tyrosinamide;
N-[N-(Phosphonomethyl)-leucyl]-N,O-dimethyl-L-tyrosinamide;
N-[N-(1-Phosphonopropyl)-leucyl]-N,O-dimethyl-L-tyrosinamide;
N-[N-(1-Phosphono-2-methylpropyl)-leucyl]-N,O-dimethyl-L-tyrosinamide; and
N-[N-(1-Phosphonoethyl)-leucyl]-N-methyl-L-tryptophanamide.

10. A compound of formula (II):

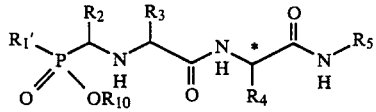

in which
$R_{10}$ is alkyl, benzyl, or benzyl substituted with a substituted selected from OH, $C_{1-6}$ alkyl, $C_{1-6}$ alkoxy or halogen,
$R_1'$ is $R_1$ or a group convertable thereto, and $R_2$, $R_3$, $R_4$ and $R_5$ are as defined for formula (I) in claim 1.

11. A pharmaceutical composition comprising a compound of formula (I) as defined in claim 1, or a pharmaceutically acceptable salt, solvate or hydrate thereof, and a pharmaceutically acceptable carrier.

12. A method of treating collagenolytic conditions in mammals which comprises administering an effective amount of a compound of formula (I) as defined in claim 1 or a pharmaceutically acceptable salt, solvate or hydrate thereof to a sufferer.

* * * * *

UNITED STATES PATENT AND TRADEMARK OFFICE
CERTIFICATE OF CORRECTION

PATENT NO. : 4,935,404

DATED : June 19, 1990

INVENTOR(S) : David James Hunter, Roger Edward Markwell, Robert William Ward

It is certified that error appears in the above-identified patent and that said Letters Patent is hereby corrected as shown below:

Claim 1, column 17, line 37, delete the word "heteroalkyl" and insert therefor --heteroaryl--.

Claim 9, column 18, line 24, delete the word "Ltyrosinamide" and insert therefor --L-tyrosinamide--.

Claim 10, column 18, line 41, replace "convertable" with --convertible--.

Signed and Sealed this

Seventeenth Day of September, 1991

Attest:

HARRY F. MANBECK, JR.

Attesting Officer

Commissioner of Patents and Trademarks